//  
United States Patent [19]

Herrmann

[11] 4,142,099

[45] Feb. 27, 1979

[54] PROCESS AND APPARATUS FOR CONTROLLING METAL THICKNESS, AND DEPOSITION AND DEGRADATION RATES

[75] Inventor: Günther Herrmann, Nuernberg-Ebensee, Fed. Rep. of Germany

[73] Assignee: Kollmorgen Technologies Corporation, Dallas, Tex.

[21] Appl. No.: 748,420

[22] Filed: Dec. 8, 1976

Related U.S. Application Data

[62] Division of Ser. No. 555,030, Mar. 3, 1975, Pat. No. 4,073,964.

[30] Foreign Application Priority Data

Mar. 5, 1974 [DE] Fed. Rep. of Germany ....... 2410927

[51] Int. Cl.² .................. G21K 7/00; G01N 23/00
[52] U.S. Cl. ....................... 250/308; 250/358 R; 427/9
[58] Field of Search ............ 250/272, 273, 277 R, 250/308, 358 R, 359, 360; 427/9

[56] References Cited

U.S. PATENT DOCUMENTS

| 3,019,336 | 1/1962 | Johns | 427/9 |
| 3,147,169 | 9/1964 | Albertson | 156/345 |
| 3,475,242 | 10/1969 | Radimer | 156/345 |
| 3,503,817 | 3/1970 | Radimer | 156/345 |
| 3,719,565 | 3/1973 | Herrmann | 204/228 |

OTHER PUBLICATIONS

IBM Technical Disclosure Bulletin, vol. 17, No. 6, Nov. 1974.

Primary Examiner—Alfred E. Smith
Assistant Examiner—Janice A. Howell
Attorney, Agent, or Firm—Morgan, Finnegan, Pine, Foley & Lee

[57] ABSTRACT

Metal layer thicknesses on articles during formation or degradation, as in electroless or electrolytic deposition or chemical etching, are measured and controlled by a process comprising determining the radiation scattering capacity of a corresponding metallic layer deposited on or removed from a test sample while the test sample is present in a bath solution during formation or degradation of the metal layer. Also provided is a novel immersible sensor for measuring the rate and thickness of metal layers being deposited or degraded.

7 Claims, 1 Drawing Figure

U.S. Patent
Feb. 27, 1979
4,142,099
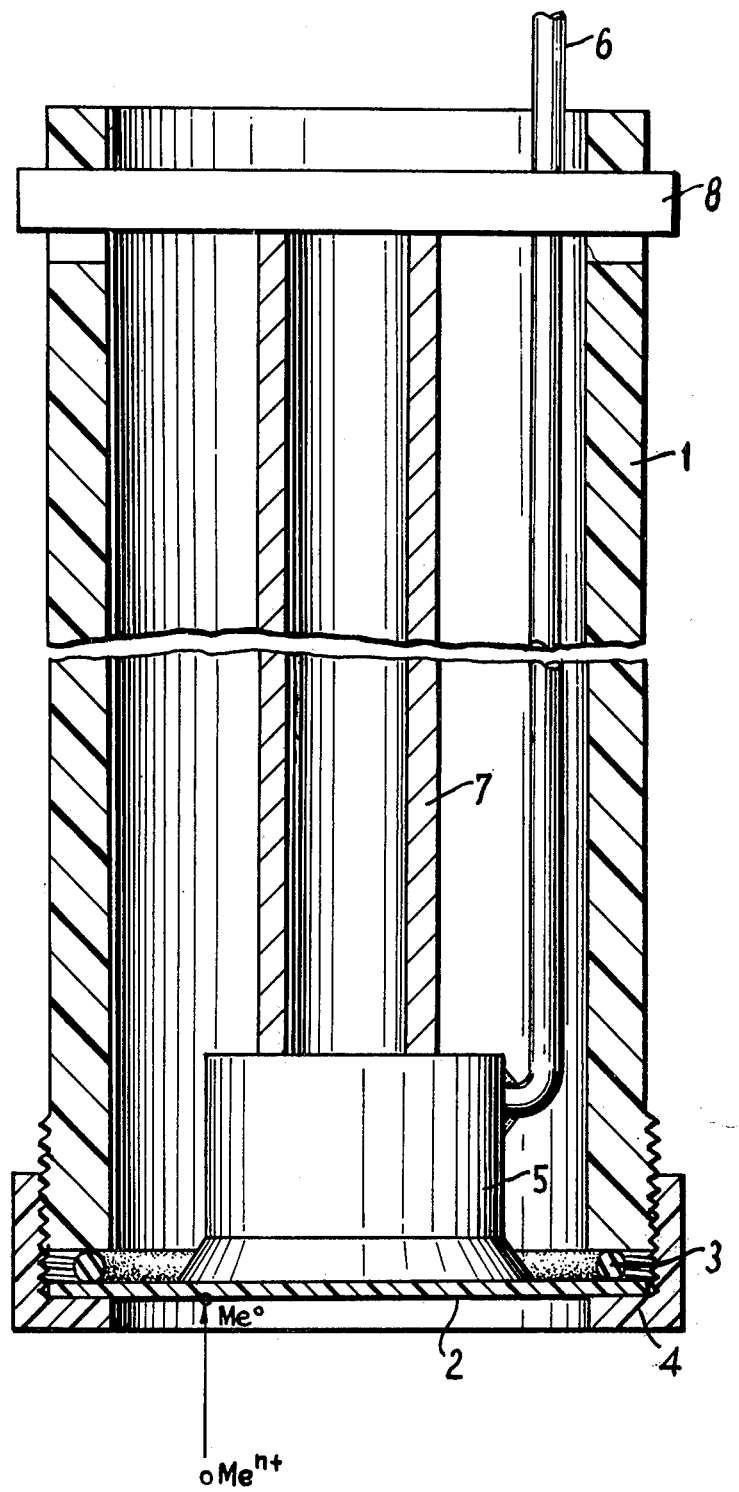

PROCESS AND APPARATUS FOR CONTROLLING METAL THICKNESS, AND DEPOSITION AND DEGRADATION RATES

This is a division of application Ser. No. 555,030 filed Mar. 3, 1975, now U.S. Pat. No. 4,073,964.

This invention relates to a process and a device for measuring metal layer thickness of coatings that are being formed or degraded on articles, such as by electroless or electrolytic deposition or chemical etching. The method is useful while the articles are present in the deposition bath, i.e., while the deposition or degradation is taking place. Furthermore, this invention relates to a method for measuring the rate at which a coating is formed or degraded in a given bath solution while said formation or degradation is taking place and using these measurements to control the deposition or degradation process.

BACKGROUND OF THE INVENTION

It is desirable to measure the layer thickness on the article being coated while it is present in the deposition bath, because this is the most practical method to obtain specific layer thicknesses reliably.

For numerous applications, the formation of a coating of a given thickness is of great importance. Falling below this layer thickness leads to performance troubles such as, for example, insufficient anti-corrosion protection or inadequate electrical properties and, therefore, to the formation of scrap. The formation of coatings with thicknesses that are greater than specified may not only lead to the formation of scrap, for instance, for mechanical tolerance reasons. In addition, the deposition process is prolonged through the formation of unnecessarily thick coatings and the amount of material used to form the coating is increased, both of which adversely affect the economics of the process. The costs arising from the formation of excessive coating thickness can be considerable such as, for example, in the production of gold platings, which are being used on a large scale as contact material in modern electrical industry. To ensure reliable contact quality, a specific, prescribed layer thickness is required. It is possible to measure easily and precisely by known processes the layer thickness of the gold plating on an object as soon as the latter has been withdrawn from the bath. If the thickness is insufficient, however, the need to return the object to the bath solution and to continue the deposition process leads to a more complicated and less economical process.

In the case of electrolytic deposition processes, using current strength to determine the quantity of metal deposited is known in the prior art. By this method, however, only the total amount of metal deposited is determined. Moreover, the geometric shape of the objects present in the deposition bath and the influence of neighboring objects and electrolysis aids (so-called pirate power consumers) cause a measurement of this kind to be of doubtful value for the determination of the layer thickness actually obtained at a given site in the deposition bath. Also, this unsatisfactory method cannot be used in the case of electroless metal deposition for determining the layer thickness before the coated article is withdrawn from the bath solution, although it is very desirable, for reasons of economy as well as of quality, to be able to know the thickness of the layer that has been formed before withdrawing the coated object from the bath solution. Another disadvantage associated with this prior art method is that the surface being coated becomes passive after being outside the bath solution for only a short time, so that it has to be reactivated if it is found that further metallization is necessary, after the coating thickness has been measured by conventional means.

With electroless metal deposition processes such as, for example, metallization by means of autocatalytic bath solutions operated without an external current supply, it is desirable for optimum operation of the deposition process to have a technique for measuring the deposition rate and its changes at any given time during the carrying out of the process. Measurement of the deposition rate while the deposition process is taking place is also advantageous both in the case of electrolytic and electrophoretic coatings.

DESCRIPTION OF THE DRAWING

The invention is better understood by reference to the drawing which shows, in elevation, a cross-sectional view of an immersible sensor according to this invention with which the methods can be carried out.

DESCRIPTION OF THE INVENTION

According to the present invention, layer thickness is measured during the deposition process by means of an immersible sensor device without removing the object being coated from the bath solution. The sensor, which can be placed anywhere in the deposition bath, consists of a casing which serves as a support for a test sample, the surface of which is being coated. The thickness of the coating being formed is measured by means of the scattering measuring method. For this purpose radiation emitted by a suitable radioactive preparation is reflected across the test sample at the applied coating. The quantity of reflected radiation is proportionate to the layer thickness at the moment of measurement. The change of the reflected radiation with time corresponds to the change with time of the layer thickness during the deposition process, i.e., the deposition rate.

The method aspect of invention comprises measuring at any given time the thickness of a coating being formed on a test sample and the deposition rate by means of the scattering measurement of a test sample which has been placed in the deposition bath solution. If the test sample consists of the same base material as the object to be metallized, the thickness of the coating formed on the test sample corresponds directly with the thickness of the coating formed on the object to be metallized. If a test sample of different base material is used, a simple relationship exists between the measurements obtained with the test sample and the coating produced on the object to be metallized. For instance, when electroless metallization is used, if the surface of the object to be metallized and of the test sample consists of the same base material and these surfaces are similarly activated for electroless metal deposition, the rates of deposition on the test sample and on the object to be metallized correspond directly to each other. If, however, a carrier made of synthetic material which has already been provided with a coating of the metal to be deposited is used as test sample material, and the object to be metallized has a surface made of synthetic material sensitized according to one of the conventional processes for electroless metal deposition, there exists during the interval of metal film formation a correlation or function between the measurements obtained and layer thickness or deposition rate of the object to be metallized. This function depends upon, and is clearly determined by, the pretreatment used for sensitizing the surface. The measuring device of the invention can also be used to determine the catalytic activity of sensitized surfaces. Starting time, i.e., the period before metal deposition is begun, and deposition rate as a function of catalytic activity prior to the formation of a complete metallic film are suitable test results for this purpose. These can be determined according to the invention in a simple manner.

With the device of this invention it is also possible to determine in a simple way certain parameters of the deposited metallic coating, e.g., its thickness, from measurements of the layer thickness and deposition rate, particularly during the interval prior to the completion of metal film formation.

DESCRIPTION OF THE PREFERRED EMBODIMENTS

Referring to the drawing, an immersible sensor which can be used with any conventional measuring apparatus (not shown) for carrying out the scattering measuring method, comprises a casing 1 consisting of a suitable acid-and/or alkali-resistant synthetic, e.g., plastic, material. Preferably, a casing is used which has as smooth and non-porous a surface as possible, in order to avoid deposition taking place on the casing itself, if electroless baths are used. Furthermore, precautions should be taken to prevent transfers of impurities from the synthetic material casing to the bath solution because this would lead to inaccurate measurements and, in certain cases, to undesirable influences on bath performance.

Test sample 2 consists of a carrier foil (shown as circular Mylar disc in the figure) which is catalytically sensitized if electroless metal is to be deposited by conventional methods. Sensitizization is accomplished, for example, by treatment with a solution of a tin (II)/palladium (II) chloride complex. In a different embodiment (not shown) of the immersed sensor of the invention, a test sample corresponding to 2 consists of a carrier foil which is coated on one side with a thin film of the metal to be deposited, e.g., copper. In any event, test sample 2 will be affixed liquid-tight to the casing by means of O-ring 3 and coupling nut 4.

Inside casing 1 is disposed measuring head 5 which, preferably, and as shown, rests directly against the interior of test sample 2 under pre-stress so that contact and defined distance are maintained even if the immersed assembly moves in the bath liquid, e.g., under the influence of strong fluid motion currents, etc. Spacing tubes 7 are one convenient means for applying the stress to measuring head 5.

In the interior of measuring head 5 there can be a conventional radiation souce in the form of a radioactive nuclide and a Geiger-Muller tube counter for the determination of the intensity of the scattered radiation. Neither is illustrated in the drawing because these are entirely conventional.

Signal lead 6 connects measuring head 5 through a suitable liquid tight fitting, e.g., Clamp 8, to a measuring apparatus (not shown) of entirely conventional design for amplification, recording, display and similar functions.

In carrying out the process according to the invention, the immersible sensor is dipped into the bath solution and remains there during the deposition of a metal coating on the object to be metallized (or removal of the metal during etching) The embodiment shown in the drawing is intended for use in electroless metal deposition baths.

The signal supplied by measuring head 5 corresponds at any given time to the layer thickness of the metal coating which has been deposited on the exterior surface of the test sample. The deposition rate can be derived from the ratio of the change of the measurement results, which is proportional to layer thickness, with time. The deposition rate can have a negative value, e.g., in the case of electrochemical or chemical layer decomposition.

The signal evaluated by the measuring apparatus can be used by means of a recorder, for instance, for visually estimating and manually controlling the deposition process. After calibration of the apparatus, the layer thickness of a coating which has been deposited can be ascertained simply and reliably, and thus the required time needed for deposition can be accurately established so that too small nor too large a layer thickness is obtained. The process of the invention also provides that the signal and its time function corresponding to the deposition rate can be used, together with other test results, such as concentration of the bath components, temperature, and the like, for automatic control of the bath and the determination of the deposition time.

An immersible sensor like that shown in the drawing can be used for taking measurements in electrolytic baths, but in such a case the test sample consists of a metal foil or an externally metallized plastic foil which is connected to the corresponding pole of a current source. The polarity depends on the problem posed, namely whether a coating is to be formed electrolytically or decomposed electrolytically. The current source used can either be the same as that used for electrolytic metallization of the article to be metallized or a separate current source can be employed, e.g., a specially stabilized source.

In another embodiment of the immersible sensor device the latter also contains, in addition to the test sample, a counter-electrode.

The process of the invention can also be used for the measurement of electrophoretic deposition.

An example of the application of the process to the control of chemical layer degradation is its use in etching processes, particularly processes for the production of etched figures of a precise etching depth.

The selection of the radioactive nuclide depends on the sample configuration, etc. For measuring the initial performance and the deposition rate in electroless copper plating baths with a low deposition rate a nuclide can be employed. The measuring range of the nuclide can range, for example, for 1 to 10 nm in the measuring head used. This type can also serve for the determination of thin layer thicknesses. For measurements with baths of rapid deposition rate or measurement of greater layer thicknesses, it is preferable to use a nuclide with a range of 5 to 100 nm. For the measurement of total layer thickness, particularly for the formation of relatively thick coatings, the measuring range will normally be between 20 and 400 nm.

I claim:
1. An immersible sensor comprising
   (i) a casing made of a material that is highly resistant to acid and/or alkali in the form of a liquidtight envelope;
   (ii) a test sample of suitable size which is mounted in an aperture in said casing in such a way that a part of said test sample faces outwards and is adapted to contact with a bath liquid when immersed therein and a second part faces the interior of said casing;

(iii) a measuring head mounted in said casing for acting both as a source of radiation and as a receiver for the radiation energy scattered by the test sample and a layer of metal thereon; and (iv) a liquid-tight signal lead within said casing for carrying a signal supplied by said measuring head to a signal display and recording apparatus located outside a bath liquid in which said sensor is immersed.

2. An immersible sensor as defined in claim 1 wherein said test sample is a plastic foil or film.

3. An immersible sensor as defined in claim 1 wherein the surface of said test sample which is adapted to contact said bath liquid is activated for electroless metal deposition.

4. An immersible sensor as defined in claim 1 wherein the surface of said test sample which is adapted to contact said bath liquid is provided with a metallic coating.

5. An immersible sensor as defined in claim 1 wherein said test sample consists of a metallic film, a metallic foil or a plastic foil.

6. An immersible sensor as defined in claim 5 which includes a counter-electrode in close coupled relationship to said test sample.

7. An immersible sensor as defined in claim 1 wherein said measuring head is in pre-stressed contact with the part of said test sample surface which faces the interior of said casing.

* * * * *